United States Patent
Décor

[11] 4,087,464
[45] May 2, 1978

[54] α-HALOGENO-ACETALS OF ETHYLENICALLY UNSATURATED ALDEHYDES AND THEIR PREPARATION

[75] Inventor: Jean-Pierre Décor, Thurins, France

[73] Assignee: Rhone-Poulenc Industries, Paris, France

[21] Appl. No.: 771,304

[22] Filed: Feb. 23, 1977

[30] Foreign Application Priority Data

Feb. 25, 1976 France .............................. 76 05243

[51] Int. Cl.² ...................... C07C 43/30; C07C 41/00
[52] U.S. Cl. ...................... 260/615 A; 260/607 AR; 260/607 AL
[58] Field of Search ...................... 260/615 A

[56] References Cited

FOREIGN PATENT DOCUMENTS 763,467  12/1956  United Kingdom ............ 260/615 A
775,358  5/1957  United Kingdom ............ 260/615 A

OTHER PUBLICATIONS

Shosta kovski et al., Chem. Abst. 53, 7002h, 1959.

Primary Examiner—Howard T. Mars
Attorney, Agent, or Firm—Stevens, Davis, Miller & Mosher

[57] ABSTRACT

α-Halogeno-acetals of ethylenically-unsaturated aldehydes of the formula:

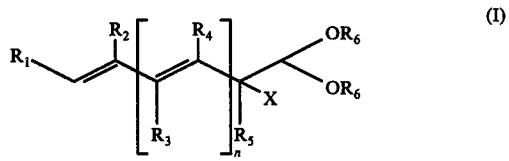

(I)

are disclosed, which are prepared by reacting a hypohalite of a saturated aliphatic tertiary alcohol with an ethylenically-unsaturated aldehyde of the formula:

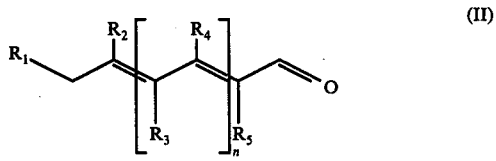

(II)

in which: $R_1$, $R_2$, $R_3$, $R_4$ and $R_5$, which may be identical or different, represent hydrogen or straight or branched alkyl of from 1 to 6 carbon atoms especially methyl or ethyl, X represents halogen, especially chlorine or bromine, $R_6$ represents straight or branched alkyl of from 1 to 6 carbon atoms especially methyl or ethyl; and $n$ represents zero or 1. Such α-halogeno acetals may be used to introduce an ethylenically-unsaturated aldehyde unit into a monoene or polyene radical.

10 Claims, No Drawings

α-HALOGENO-ACETALS OF ETHYLENICALLY UNSATURATED ALDEHYDES AND THEIR PREPARATION

The present invention provides α-halogeno-acetals of ethylenically unsaturated aldehydes of the formula:

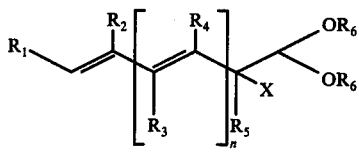
(I)

in which: $R_1$, $R_2$, $R_3$, $R_4$ and $R_5$, which may be identical or different, represent hydrogen or straight or branched alkyl of from 1 to 6 carbon atoms especially methyl or ethyl, X represents halogen, especially chlorine or bromine, $R_6$ represents straight or branched alkyl of from 1 to 6 carbon atoms, especially methyl or ethyl, and $n$ represents zero or 1; and a process for their preparation.

It is already known to prepare γ-halogeno-acetals of ethylenically α,β-unsaturated aldehydes by halogeno-alkylation of 1-alkoxy-1,3-dienes with N-halogeno-succinimides in the presence of an alcohol, in accordance with the process described by S. M. MAKIN et al., J. Gen. Chem. U.S.S.R. 32, 1088 (1962). However, the literature does not provide any examples of the preparation of α-halogeno-acetals from ethylenically unsaturated aldehydes.

According to the present invention, the compounds of the formula (I) are prepared by a process which comprises reacting a hypohalite of a saturated aliphatic tertiary alcohol with an ethylenically unsaturated aldehyde of the formula:

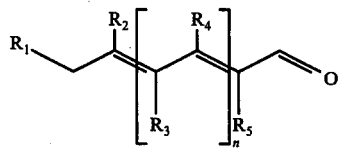
(II)

in which $R_1$, $R_2$, $R_3$, $R_4$, $R_5$ and $n$ are as defined above, in the presence of a saturated aliphatic primary alcohol of the formula $R_6OH$, in which $R_6$ is as defined above.

The hypohalite of a saturated aliphatic tertiary alcohol used in the process of the invention is preferably a bromine or chlorine derivative. The hypohalite of tert.-butanol is preferred for reasons of ease of availability. However, the hypohalites of higher saturated, tertiary, aliphatic alcohols of up to 13 carbon atoms are also suitable. Generally, the hypohalite is used as a solution in an organic solvent which is inert under the reaction conditions, such as a liquid lower aliphatic hydrocarbon, for example pentane; an aromatic hydrocarbon for example benzene, toluene or a xylene; or a halogenated aliphatic or aromatic hydrocarbon.

The temperature of the reaction is not critical and can, for example, be between −40° and +80° C. Preferably, the reaction is carried out at a temperature below 0° C, for example at −20° C, in order to avoid appreciable decomposition of the reagent.

Generally, the quantities of the hypohalite and of the aldehyde of the formula (II), are close to the stoichiometric quantities. However, an excess of one or other of these reagents can be used without disadvantage. Usually it is sufficient to use a stoichiometric quantity of the alcohol of the formula $R_6OH$. It is, however, preferable to use an excess of this reagent so that it may serve as the reaction medium.

In order to speed up the reaction rate, it is advantageous to carry out the reaction in the presence of a catalytic quantity of a strong inorganic acid which is known as a catalyst for acetal formation, such as hydrochloric acid or sulphuric acid. This acid may be introduced into the reaction mixture either at the start of the reaction or after the reaction of the hypohalite with the aldehyde of the formula (II).

The monoene and diene aldehydes of the formula (II) are compounds which either are known or can be prepared using known methods. The α-halogen-acetals of the formula (I) are intermediates which can be used in organic synthesis. For example, they can be used to introduce an ethylenically unsaturated aldehyde unit into a monoene or polyene radical. More specifically the compounds of the formula (I) are starting materials used in the preparation of the compounds of the formula:

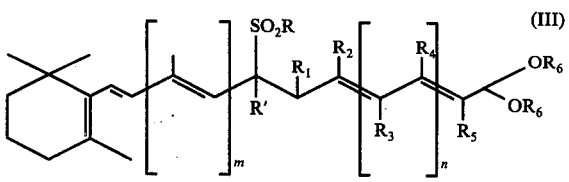
(III)

in which $R_1$, $R_2$, $R_3$, $R_4$, $R_5$, $R_6$ and $n$ are as defined above, $m$ and $n$ represent zero or 1 such that $m + n = 1$, R represents straight or branched alkyl of from 1 to 6 carbon atoms, or arylalkyl containing a straight or branched alkyl of from 1 to 6 carbon atoms, or aryl such as phenyl, unsubstituted or substituted by straight or branched alkyl preferably of from 1 to 6 carbon atoms, straight or branched alkoxy preferably of from 1 to 6 carbon atoms, straight or branched alkylthio preferably of from 1 to 6 carbon atoms, straight or branched alkoxycarbonyl such that the alkoxy is preferably of from 1 to 6 carbon atoms, hydroxyl or halogen, and R' represents hydrogen or, if $m$ is zero, straight or branched alkyl of from 1 to 6 carbon atoms, especially methyl or ethyl.

The compounds of the formula (III) are known, see, for example, Belgian Pat. Nos. 794,872 and 807,036. They are starting materials for the preparation of polyene compounds of the terpene, geraniolene and sesquiterpene series. Desulphonation of the compounds of the formula (III) by treatment with an organic or inorganic basic reagent allows a further ethylenic double bond to be introduced into the aliphatic chain. Again, see, for example, Belgian Pat. Nos. 794,872 and 807,036.

The preparation of the compounds of the formula (III) from the compounds of the formula (I) can be carried out by reacting an α-halogeno-acetal of the formula (I) with a sulphone of the formula:

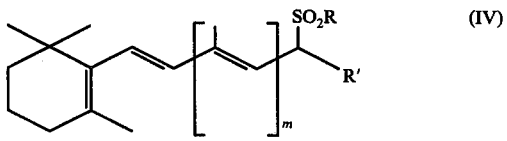
(IV)

in which R and R' are as defined above and m is zero or 1, depending on the meaning of the symbol n in the starting material of the formula (I) used, such that $m + n = 1$.

The reaction is preferably carried out in a basic polar aprotic solvent and in the presence of a basic agent having sufficient activity to anionise the sulphone employed. Dimethylformamide, dimethylacetamide, dimethylsulphoxide, N-methylpyrrolidone and hexamethylphosphotriamide are particularly suitable as basic polar aprotic solvents. The basic reagents which are suitable are inorganic or organic compounds such as alkali metal alcoholates, alkali metal hydrides or amides and organometallic compounds such as organo-zinc, organo-lithium and organo-magnesium compounds. They may be used alone or conjointly with another basic reagent intended to neutralise the hydracid formed. In the case where the anion-producing reagent is used alone, the quantity employed must be sufficient to ensure this neutralisation. This quantity is also dependent on the circumstances of use and on the reactivity of the reaction products with respect to this basic reagent. For these various reasons, it may be advantageous to introduce a lesser quantity of anion-producing reagent into the reaction mixture and to add another basic reagent, with respect to which the products of the reaction are less sensitive and which is sufficient to neutralise the hydracid formed.

The reaction can be carried out at temperatures of between $-100°$ C and $+150°$ C, depending on the nature of the starting materials and products, and preferably under an inert atmosphere, for example under argon.

The compounds of the formula (III) can be de-acetalised to the corresponding aldehyde sulphones of the formula:

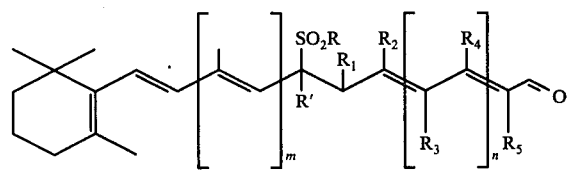

in which the symbols are as defined above, the said aldehydes being themselves compounds which are disclosed in Belgian Pat. Nos. 794,872 and 807,036. This de-acetalisation can be carried out by any method known in itself for the de-acetalisation of analogous compounds. Generally, the de-acetalisation is carried out by the action of an excess of water, at a pH equal to or less than 7 and at a temperature of between $-40°$ and $+80°$ C, preferably between $-20°$ and $+20°$ C. Generally, it is not necessary to isolate the acetal sulphone of the formula (I) in order to effect the de-acetalisation. This conversion can be effected directly on the crude product of the reaction between an α-halogeno-acetal of the formula (I) and a sulphone of the formula (IV).

The sulphones of the formula (IV) are known, their preparation is in particular described in Belgian Pat. Nos. 794,872 and 807,036.

The preparation of the compounds of formula (III) is described and claimed in Application Ser. No. 771815, filed Feb. 23, 1977 entitled "Process for the preparation of acetal sulphones".

The compounds of the formula (I), in which X represents chlorine or bromine and n is zero, $R_1$, $R_3$, $R_4$ and $R_5$ represent hydrogen and $R_2$ represents methyl; or n is equal to 1, $R_1$, $R_2$, $R_3$ and $R_5$ represent hydrogen and $R_4$ represents methyl, are of particular interest. By their action on a sulphone of the formula (IV) in which, respectively: m is 1 and R' represents hydrogen, and m is zero and R' represents methyl; products of the formula (III) which constitute precursors for vitamin A are formed.

The following Examples illustrate the present invention and the use of the compounds of the formula (I).

EXAMPLE 1

One drop of concentrated sulphuric acid is added to a solution of 8.40 g (0.1 mol) of 3-methyl-2-butenal (otherwise called prenal) in 84 cm³ of methanol cooled to $-20°$ C, followed by 45.5 cm³ of a 2.20 molar solution of tert.-butyl hypochlorite in pentane which is added over a period of 90 minutes. The temperature is then allowed to rise to 0° C over a period of 30 minutes. The reaction mixture is then poured into 150 cm³ of water containing 12.6 g (0.1 mol) of sodium bicarbonate. The aqueous phase is separated off and extracted 3 times with a total of 75 cm³ of pentane. The organic phases are combined, washed with 30 cm³ of water and then with 30 cm³ of a saturated aqueous sodium bicarbonate solution and dried over anhydrous sodium carbonate. After concentrating to dryness under reduced-pressure of about 20 mm of mercury at a temperature below 50° C, 15.42 g of a residue consisting of a mixture of 2-chloro-1,1-dimethoxy-3-methyl-3-butene (6.74 × $10^{-2}$ mols), and 2-chloro-1,1,3-trimethoxy-3-methylbutane (2.25 × $10^{-2}$ mols), which are identified by nuclear magnetic resonance, are obtained. 9.4 g of 2-chloro-1,1,-dimethoxy-3-methyl-3-butene, b.p., 36°–36.5° C, 0.2 mm Hg, are obtained by distillation.

The solution of tert.-butyl hypochlorite in pentane can be prepared in the following way:

A mixture of 44.7 g (0.6 mol) of tert.-butanol and 40 g (0.666 mol) of acetic acid is added at 2°–4° C and over a period of 7 minutes to 780 cm³ of an aqueous sodium hypochlorite solution containing 0.6 mol of NaOCl. After completion of the addition, the reaction mixture is maintained at 4° C for 8 minutes and then extracted with 50 cm³ of pentane. The organic extract is washed with 50 cm³ of saturated aqueous sodium bicarbonate solution and then with 50 cm³ of water, dried over calcium chloride and then made up to 100 cm³ by the addition of pentane. 100 cm³ of a 4.42 molar solution of tert.-butyl hypochlorite in pentane are thus obtained; a 2.20 molar solution is obtained by dilution to 200 cm³.

EXAMPLE 2

1.6 cm³ of concentrated sulphuric acid are added to a solution of 5.04 g (6 × $10^{-2}$ mols) of 3-methyl-2-butenal (otherwise called prenal) in 50 cm³ of methanol cooled to $-20°$ C, followed by 77.5 cm³ of a 0.774 molar solution of tert.-butyl hypobromite in pentane which is added over a period of 90 minutes. The temperature is then allowed to rise to 0° C. over a period of 30 minutes. The reaction mixture is then poured into 100 cm³ of water containing 11.16 g (0.9 × $10^{-2}$ mol) of sodium bicarbonate. The aqueous phase is separated off and extracted 3 times with a total of 75 cm³ of pentane. The organic phases are combined, washed with 30 cm³ of water and then with 30 cm³ of a saturated aqueous sodium bicarbonate solution and dried over anhydrous sodium carbonate. After concentrating to dryness under reduced pressure of about 20 mm of mercury at a temperature below 50° C, 12.92 g of a residue consisting of a mixture of 2-bromo-1,1-dimethoxy-3-methyl-3-butene and 2-bromo-1,1,3-trimethoxy-3-methyl-butane, which are identified by nuclear magnetic resonance, are obtained. 6.55 g of 2-bromo-1,1-dimethoxy-3-methyl-3-butene, b.p. = 48.5° C 0.2 mm Hg are obtained by distillation.

The solution of tert.-butyl hypobromite in pentane can be prepared by the method described by C. WALLING, J. Org. Chem., 27, 2976 (1962).

EXAMPLE 3

A solution of 3.44 of phenyl 5-(2,6,6-trimethyl-1-cyclohexenyl)-3-methyl-2,4-pentadienyl sulphone of 94% purity (1.1 × 10$^{-2}$ mols) in 5.74 cm$^3$ of N-methylpyrrolidone is added at −20° C, under an atmosphere of argon, over a period of 5 minutes, to a mixture of 1.055 g (1.1 × 10$^{-2}$ mols) of sodium tert.-butylate in 4.95 cm$^3$ of N-methylpyrrolidone. After stirring for 5 minutes at −20° C, a solution of 2.368 g (1.135 mols) of 2-bromo-1,1-dimethoxy-3-methyl-3-butene in 4.5 cm$^3$ of N-methylpyrrolidone is added over a period of 1 hour. The reaction mixture is then stirred at 0° C for 2 ¼ hours, followed by the addition of 12 cm$^3$ of diisopropyl ether, from which the peroxides have been removed, and 25 cm$^3$ of water, successively over a period of 10 minutes. The aqueous phase is extracted twice with a total of 20 cm$^3$ of diisopropyl ether. The organic phases are combined. A solution of 1,1-dimethoxy-3,7-dimethyl-9-(2,6,6-trimethyl-1-cyclohexenyl)-2,6,8-nonatrienyl-5-phenylsulphone is thus obtained which can be converted directly to the corresponding aldehyde by proceeding in the following manner.

The solution obtained above is stirred at 20° C for about 1 ¾ hours with 0.247 cm$^3$ of a 4 N aqueous sulphuric acid solution, then washed successively with 5 cm$^3$ of a saturated aqueous sodium bicarbonate solution and twice with a total of 5 cm$^3$ of water, and finally dried over anhydrous sodium sulphate. After filtering and cooling at 0° C for 15 minutes, 0.6275 g of a product identified by nuclear magnetic resonance as 3,7-dimethyl-9-(2,6,6-trimethyl-1-cyclohexenyl)-1-oxo-2,6,8-nonatrienyl-5-phenylsulphone is filtered off.

By concentrating the mother liquors of the above product, a residue weighing 3.970 g is obtained which contains, as measured by nuclear magnetic resonance, 8.12 × 10$^{-3}$ mols of 3,7-diemthyl-9-(2,6,6-trimethyl-1-cyclohexenyl)-1-oxo-2,6,8-nonatrienyl-5-phenylsulphone and 0.53 × 10$^{-3}$ mol of starting phenyl 5-(2,6,6-trimethyl-1-cyclohexenyl)-3-methyl-2,4-pentadienyl sulphone. The yield of aldehyde sulphone is 91% relative to the starting sulphone consumed.

I claim

1. An α-halogeno-acetal of an ethylenically unsaturated aldehyde corresponding to the formula:

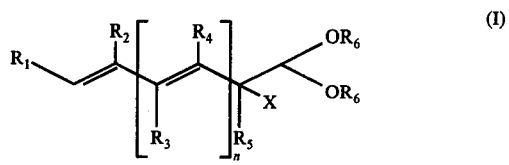

in which: R$_1$, R$_2$, R$_3$, R$_4$ and R$_5$, which may be identical or different, represent hydrogen or straight or branched alkyl of from 1 to 6 carbon atoms, X represents chlorine or bromine, R$_6$ represents straight or branched alkyl of from 1 to 6 carbon atoms, and n represents zero or 1.

2. An α-halogeno-acetal according to claim 1, in which R$_1$, R$_3$, R$_4$ and R$_5$ each represent hydrogen, R$_2$ represents methyl and n is zero.

3. An α-halogeno-acetal according to claim 1, in which R$_1$, R$_2$, R$_3$ and R$_5$ each represent hydrogen, R$_4$ represents methyl and n is 1.

4. 2-Chloro-1,1-dimethoxy-3-methyl-3butene.

5. 2-Bromo-1,1-dimethoxy-3-methyl-3-butene.

6. Process for the preparation of an α-halogeno-acetal of an ethylenically unsaturated aldehyde as claimed in claim 1, which comprises reacting a hypochlorite or hypobromite of a saturated aliphatic tertiary alcohol with an ethylenically unsaturated aldehyde of the formula:

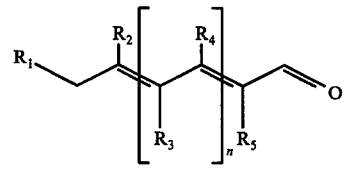

in which R$_1$, R$_2$, R$_3$, R$_4$ and R$_5$ are as defined in claim 1, at a temperature between −40° and +80° C in the presence of a saturated aliphatic primary alcohol of the formula R$_6$OH, in which R$_6$ is as defined in claim 1.

7. Process according to claim 6, in which the reaction takes place in the presence of a catalytic quantity of a strong inorganic acid.

8. Process according to claim 6, in which the hypochlorite or hypobromite is of a saturated aliphatic tertiary alcohol of 4 to 13 carbon atoms.

9. Process according to claim 6, in which the hypochlorite or hypobromite is used as a solution in an inert organic solvent.

10. Process according to claim 8, in which tert.-butyl hypochlorite or hypobromite is used.

* * * * *